United States Patent
Jermy et al.

(10) Patent No.: US 10,661,260 B2
(45) Date of Patent: May 26, 2020

(54) ZEOLITE COMPOSITE CATALYSTS FOR CONVERSION OF HEAVY REFORMATE TO XYLENES

(71) Applicants: King Fahd University of Petroleum and Minerals, Dhahran (SA); Saudi Arabian Oil Company, Dhahran (SA)

(72) Inventors: Balasamy Rabindran Jermy, Dhahran (SA); Syed Ahmed Ali, Dhahran (SA); Raed Hasan Abudawoud, Al-Khobar (SA); Abdullah Mohammed Aitani, Al-Khobar (SA); Sulaiman Saleh Al-Khattaf, Dhahran (SA)

(73) Assignees: King Fahd University of Petroleum and Minerals, Dhahran (SA); Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/624,090

(22) Filed: Jun. 15, 2017

(65) Prior Publication Data
US 2018/0361365 A1    Dec. 20, 2018

(51) Int. Cl.
*B01J 29/80* (2006.01)
*B01J 29/72* (2006.01)
(Continued)

(52) U.S. Cl.
CPC .......... *B01J 29/80* (2013.01); *B01J 29/7007* (2013.01); *B01J 29/7215* (2013.01);
(Continued)

(58) Field of Classification Search
None
See application file for complete search history.

(56) References Cited

U.S. PATENT DOCUMENTS

| | | | |
|---|---|---|---|
| 4,861,739 A * | 8/1989 | Pellet | B01J 29/005 502/64 |
| 6,558,647 B2 | 5/2003 | Lacombe et al. | |

(Continued)

FOREIGN PATENT DOCUMENTS

| | | | |
|---|---|---|---|
| CN | 103626655 | * | 3/2014 |
| WO | 2006/070073 A1 | | 7/2006 |

(Continued)

OTHER PUBLICATIONS

Huang, Limin, et al. "Investigation of Synthesizing MCM-41/ZSM-5 Composites". J. Phys. Chem. B. 104. 2817-2823 (2000). (Year: 2000).*

(Continued)

*Primary Examiner* — Sheng H Davis
(74) *Attorney, Agent, or Firm* — Dinsmore & Shohl LLP

(57) ABSTRACT

Embodiments of zeolite composite catalysts and methods of producing the zeolite composite catalysts are provided, where the methods comprise dissolving in an alkaline solution a catalyst precursor comprising at least one mesoporous zeolite while heating, stirring, or both to yield a dissolved zeolite solution, where the mesoporous zeolite has a molar ratio of $SiO_2/Al_2O_3$ of at least 30, where the mesoporous zeolite comprises zeolite beta, adjusting the pH of the dissolved zeolite solution, aging the pH adjusted dissolved zeolite solution to yield solid zeolite composite from the dissolved zeolite solution, and calcining the solid zeolite composite to produce the zeolite composite catalyst, where the zeolite composite catalyst has a mesostructure comprising at least one disordered mesophase and at least one ordered mesophase, and where the zeolite composite catalyst has a surface area defined by the Brunauer-Emmett-Teller (BET) analysis of at least 600 $m^2/g$.

20 Claims, 9 Drawing Sheets

(51) Int. Cl.

| | | |
|---|---|---|
| *B01J 35/10* | (2006.01) | |
| *C01B 39/02* | (2006.01) | |
| *C07C 6/12* | (2006.01) | |
| *B01J 29/70* | (2006.01) | |
| *B01J 37/00* | (2006.01) | |
| *B01J 37/02* | (2006.01) | |
| *B01J 37/04* | (2006.01) | |
| *B01J 37/08* | (2006.01) | |
| *C07C 6/06* | (2006.01) | |
| *B01J 29/74* | (2006.01) | |
| *B01J 29/78* | (2006.01) | |

(52) U.S. Cl.
CPC ....... *B01J 35/1019* (2013.01); *B01J 35/1023* (2013.01); *B01J 35/1042* (2013.01); *B01J 35/1047* (2013.01); *B01J 35/1057* (2013.01); *B01J 35/1061* (2013.01); *B01J 37/0018* (2013.01); *B01J 37/0201* (2013.01); *B01J 37/04* (2013.01); *B01J 37/08* (2013.01); *C01B 39/026* (2013.01); *C07C 6/06* (2013.01); *C07C 6/126* (2013.01); *B01J 29/74* (2013.01); *B01J 29/7415* (2013.01); *B01J 29/78* (2013.01); *B01J 29/7815* (2013.01); *B01J 2229/14* (2013.01); *B01J 2229/186* (2013.01); *B01J 2229/22* (2013.01); *B01J 2229/34* (2013.01); *B01J 2229/38* (2013.01); *B01J 2229/42* (2013.01); *C07C 2529/70* (2013.01); *C07C 2529/72* (2013.01); *C07C 2529/74* (2013.01); *C07C 2529/78* (2013.01); *C07C 2529/80* (2013.01)

(56) References Cited

U.S. PATENT DOCUMENTS

| | | | |
|---|---|---|---|
| 7,393,989 | B2 | 7/2008 | Negiz et al. |
| 7,589,041 | B2 | 9/2009 | Ying et al. |
| 7,799,961 | B2 | 9/2010 | Clark et al. |
| 7,803,977 | B2 | 9/2010 | Riley et al. |
| 7,807,132 | B2 | 10/2010 | Garcia-Martinez |
| 7,919,421 | B2 | 4/2011 | Kalyanaraman et al. |
| 7,951,986 | B2 | 5/2011 | Clark et al. |
| 7,976,696 | B2 | 7/2011 | Ying et al. |
| 8,071,828 | B2 | 12/2011 | Cao et al. |
| 8,329,973 | B2 | 12/2012 | Inui et al. |
| 8,435,909 | B2 | 5/2013 | Ai-Khattaf et al. |
| 8,653,315 | B2 | 2/2014 | Ali |
| 8,697,593 | B2 | 4/2014 | Ai-Khattaf et al. |
| 8,821,714 | B2 | 9/2014 | Chaumonnot et al. |
| 9,221,037 | B2 | 12/2015 | Ercan et al. |
| 9,573,121 | B2 | 2/2017 | Garcia-Martinez |
| 9,724,680 | B2 * | 8/2017 | Lai ........................ B01J 29/703 |
| 9,963,349 | B2 | 5/2018 | Boorse et al. |
| 2004/0138051 | A1 * | 7/2004 | Shan ........................ B01J 21/06 502/60 |
| 2005/0234279 | A1 | 10/2005 | Serra et al. |
| 2007/0244347 | A1 | 10/2007 | Ying et al. |
| 2008/0214882 | A1 | 9/2008 | Pinnavaia et al. |
| 2011/0118107 | A1 * | 5/2011 | Garcia-Martinez ...... B01J 29/04 502/62 |
| 2011/0201860 | A1 | 8/2011 | Akhtar et al. |
| 2012/0258852 | A1 | 10/2012 | Martinez et al. |
| 2013/0090507 | A1 | 4/2013 | Ali |
| 2013/0165315 | A1 * | 6/2013 | Al-Khattaf ............ C01B 39/023 502/69 |
| 2013/0281750 | A1 | 10/2013 | Abudawoud |
| 2014/0128246 | A1 | 5/2014 | Garcia-Martinez |
| 2015/0086786 | A1 * | 3/2015 | Itabashi .................. C01B 39/46 428/402 |
| 2015/0182953 | A1 * | 7/2015 | Senderov ................. B01J 29/83 423/714 |
| 2016/0220987 | A1 | 8/2016 | Lai et al. |
| 2017/0157598 | A1 | 6/2017 | Chal et al. |
| 2018/0185827 | A1 | 7/2018 | Cheng et al. |

FOREIGN PATENT DOCUMENTS

| | | | |
|---|---|---|---|
| WO | 2011047528 | A1 | 4/2011 |
| WO | 2013123299 | A1 | 8/2011 |
| WO | 2013151689 | A1 | 10/2013 |
| WO | 2013154086 | * | 10/2013 |
| WO | 2017060464 | A1 | 4/2017 |
| WO | 2013154086 | * | 10/2017 |

OTHER PUBLICATIONS

Xu, H et al., "Synthesis of Beta/MCM-41 composite molecular sieve with high hydrothermal stability in static and stirred condition" Journal of Colloid and Interface Science, Jan. 15, 2009, pp. 346-350, vol. 329, No. 2, Academic Press, Inc., US.

Zhang, H et al., "Preparation and characterization of Beta/MCM-41 composite zeolite with a stepwise-distributed pore structure" Powder Technology, Nov. 21, 2007, pp. 73-78, vol. 183, No. 1, Elsevier Sequoia, CH.

International Search Report and Written Opinion pertaining to International Application No. PCT/US2018/036269 dated Nov. 12, 2018.

Odedairo et al. "Aromatic transformations over aluminosilicate micro/mesoporous composite materials", Catalysis Science & Technology, vol. 2, No. 6, Jan. 1, 2012, pp. 1275-1286, United Kingdom.

Li, et al., "Synthesis of hierarchical mesoporous zeolites based on MOR zeolite: application in the automobile tailpipe hydrocarbon trap", Journal of Porous Materials, vol. 22, No. 3, Apr. 2, 2015, pp. 807-815, Netherlands.

International Search Report and Written Opinion pertaining to International Application No. PCT/US2018/028798 dated Sep. 19, 2018.

* cited by examiner

ZEOLITE COMPOSITE CATALYSTS FOR CONVERSION OF HEAVY REFORMATE TO XYLENES

TECHNICAL FIELD

Embodiments of the present specification generally relate to zeolite composite catalysts, and specifically relate to zeolite composite catalysts and methods of using the same to convert heavy reformate to xylenes.

BACKGROUND

Aromatic hydrocarbon compounds derived from petrochemical sources, benzene ($C_6H_6$), toluene (methylbenzene, $C_7H_8$), and xylenes (dimethylbenzenes, $C_8H_{10}$ isomers) may be used as starting materials for a wide range of consumer products. The xylenes include three isomers of dimethylbenzene, namely: 1,2-dimethylbenzene (ortho-xylene or o-xylene), 1,3-dimethylbenzene (meta-xylene or m-xylene), and 1,4-dimethylbenzene (para-xylene or p-xylene). The three isomers of xylene may be used in the synthesis of a number of useful products. For example, upon oxidation, the p-xylene isomer yields terephthalic acid, which may be used in the manufacture of polyester plastics and synthetic textile fibers (such as Dacron), films (such as Mylar), and resins (such as polyethylene terephthalate, used in making plastic bottles). The m-xylene isomer may be used in the manufacture of plasticizers, azo dyes, and wood preservers, for example. The o-xylene isomer may be used as a feedstock for phthalic anhydride production, which in turn may be used to make polyesters, alkyl resins, and PVC plasticizers. Therefore, the demand for xylenes remains strong as markets for polyester fibers and polyethylene terephthalate continue to demonstrate high growth rates.

Environmental regulations in several countries limit the amount of aromatics that can be blended into the gasoline pool. Most of the aromatics in gasoline originate from catalytic reforming of naphtha. Aromatic hydrocarbon compounds contained in a gasoline generally have higher octane values and are superior as a gasoline base, because of their high calorific values. Among them, toluene and aromatic hydrocarbon compounds, especially those having eight carbon atoms, have higher octane values and drivability levels, thus, it is desirable to increase the volume of $C_8$ aromatic compounds in gasoline. Light reformate of the naphtha is blended into gasoline, because it has a high octane number and lower boiling point; however, environmental regulations exclude a substantial quantity of the heavy reformate in gasoline, thus making heavy reformates available for utilization elsewhere.

Typically, heavy reformate contains 90 weight (wt.) % to 95 wt. % $C_9$ and 5 wt. % to 10 wt. % $C_{10}$ aromatic compounds. Among the $C_9$ components, trimethylbenzenes (TMBs) (50 wt. % to 60 wt. %) and methylethylbenzenes (MEBs) (30 wt. % to 40 wt. %) are the major constituents. One of the economically viable options is to convert the heavy aromatics in the heavy reformate into valuable products, such as xylenes. Demand is growing faster for xylene derivatives than for benzene derivatives. Therefore, a higher yield of xylenes at the expense of benzene yield is a favorable objective.

Heavy reformate can be subjected to transalkylation either alone or with $C_7$ (toluene) for the production of xylenes ($C_8$) and benzene ($C_6$). Because many different compounds may be present in the heavy reformate, multiple parallel and consecutive reactions may take place. Transalkylation reactions for converting aromatic hydrocarbon compounds to compounds having a different number of carbon atoms may include the disproportionation reaction of toluene, i.e., two molecules of toluene react to form one molecule of benzene and one molecule of xylene (by transfer of a methyl group from one molecule of toluene to the other, a transalkylation reaction). Transalkylation reactions, however, are not limited to the disproportionation of toluene. Other methods of increasing xylene yields operate through inducing transalkylation by adding aromatic hydrocarbon compounds having nine or more carbon atoms into the starting materials, resulting in such reactions as the addition of one mole of toluene to one mole of a $C_9$ aromatic hydrocarbon to produce two moles of xylene. These parallel and consecutive reaction methodologies may also be accompanied by multiple chemical equilibria, including isomerization of xylenes, TMBs and MEBs. The transalkylation and disproportionation reactions are equilibrium constrained, while the dealkylation reactions are kinetically controlled.

It is also known to separate isomers through molecular sieves formed by zeolites. Zeolites are generally hydrated aluminum and calcium (or sodium) silicates that can be made or selected with a controlled porosity for catalytic cracking in petroleum refineries, and may be natural or synthetic. The pores may form sites for catalytic reactions to occur, and may also form channels that are selective for the passage of certain isomers to the exclusion of others. Zeolites may serve as Brönsted acids for hydrogen ion exchange by washing with acids, or as Lewis acids by heating to eliminate water from the Brönsted sites. For example, the zeolite ZSM-5 ($Na_3Al_3Si_{93}O_{192}.16H_2O$) has a pore size that results in the formation of channels of such size and shape that it forms a selective sieve for xylene isomers. The alkylation of toluene by methanol will form a mixture of all three xylene isomers. p-Xylene will pass through the channels in ZSM-5 due to its linear configuration, while o-xylene and m-xylene will not pass through the pores, although they may subsequently rearrange to p-xylene under the acidic conditions in the pores and then pass through the sieve. The catalytic activity of zeolites can also be increased by addition of a metal catalyst that activates hydrogen by breaking up molecular hydrogen to atomic hydrogen on the surface of the metal for forming intermediates in transalkylation reactions.

Regardless, these conventional means to produce xylenes by fractionation of reformate results in a xylene yield that is insufficient to meet the demand, and conversion of other hydrocarbons is necessary to increase the yield of xylenes. Furthermore, xylene isomer streams from catalytic reforming or other sources do not meet the demand as chemical intermediates. Para-xylene in particular is a major chemical intermediate with rapidly growing demand, but equates to only 20% to 25% of a typical $C_8$ aromatics stream.

SUMMARY

Accordingly, ongoing needs exist for catalysts suitable for converting heavy reformates to produce xylenes. Embodiments of the present disclosure are related to zeolite composite transalkylation catalysts, their preparation methods and performance, particularly to the synthesis of such catalysts having an ordered/disordered mesostructure and hydrothermal stability. The zeolite composite catalysts may convert a mixture of heavy aromatic compounds, particularly $C_9$ aromatic hydrocarbons to benzene, toluene, and xylenes, and particularly to commercially valuable xylenes. The conversion reactions include dealkylation, transalkylation, disproportionation and isomerization. The zeolite composite catalysts have a high ethyl-dealkylation activity as well as high methyl-transalkylation activity to improve the yield of xylenes.

According to one embodiment, a method of producing a zeolite composite catalyst is provided. The method comprises dissolving in an alkaline solution a catalyst precursor comprising mesoporous zeolite while heating, stirring, or both to yield a dissolved zeolite solution, where the mesoporous zeolite has a molar ratio of $SiO_2/Al_2O_3$ of at least 30, where the mesoporous zeolite comprises zeolite beta, adjusting the pH of the dissolved zeolite solution, aging the pH adjusted dissolved zeolite solution to yield solid zeolite composite from the dissolved zeolite solution, and calcining the solid zeolite composite to produce the zeolite composite catalyst, where the zeolite composite catalyst has a mesostructure comprising at least one disordered mesophase and at least one ordered mesophase, and where the zeolite composite catalyst has a surface area defined by a Brunauer-Emmett-Teller (BET) analysis of at least 600 $m^2/g$.

According to another embodiment, a zeolite composite catalyst is provided. The zeolite composite catalyst comprises a mesostructure comprising at least one disordered mesophase and at least one ordered mesophase, where the zeolite composite catalyst has a surface area defined by the Brunauer-Emmett-Teller (BET) analysis of at least 600 $m^2/g$ and where the zeolite composite catalyst comprises zeolite beta.

According to yet another embodiment, a method of converting $C_{9+}$ alkyl aromatic hydrocarbons to a product stream comprising benzene, toluene, and xylene is provided. The method comprises reducing a zeolite composite catalyst comprising a mesostructure comprising at least one disordered mesophase and at least one ordered mesophase, where the zeolite composite catalyst has a surface area defined by BET of at least 600 $m^2/g$ with hydrogen gas at 400° C., where the zeolite composite catalyst comprises zeolite beta. The method further comprising contacting a feed comprising $C_{9+}$ alkylaromatic hydrocarbons with the reduced composite zeolite catalyst and hydrogen in a transalkylation zone of a reactor to produce a transalkylation product, stripping $C_1$-$C_5$ and lighter hydrocarbons and stripping unreacted feed from the transalkylation product, and collecting xylenes product from the transalkylation product.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Figure 9:
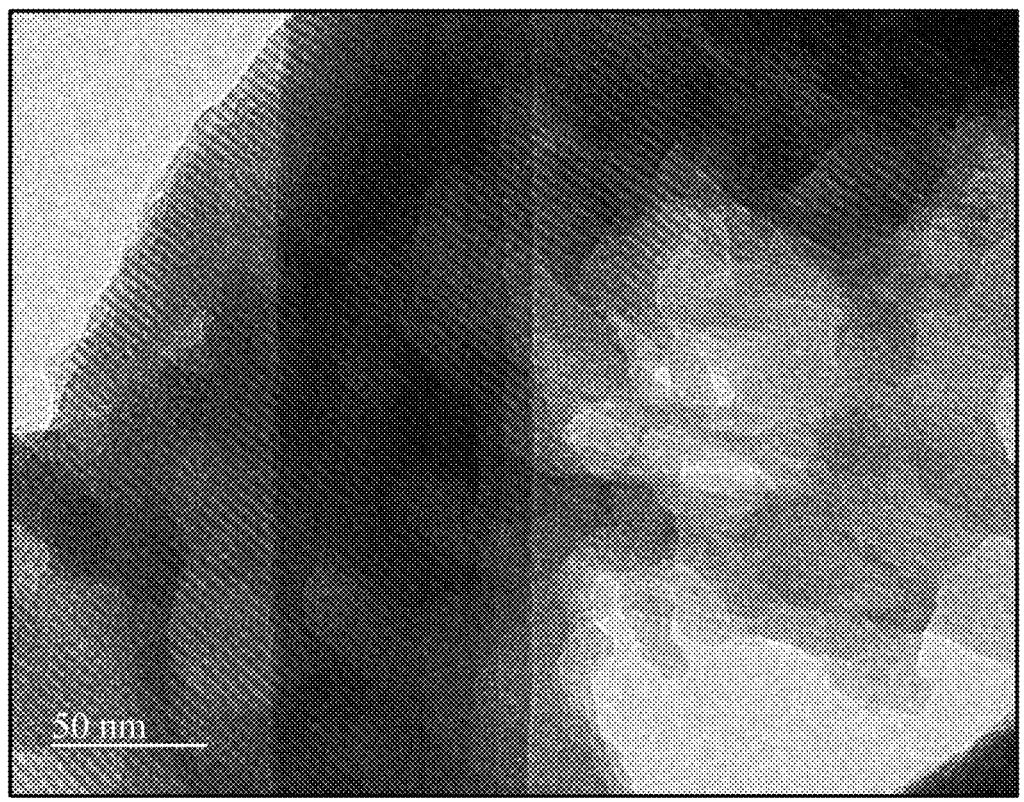
FIG. 9 is a TEM image showing ordered hexagonal phase and disordered hexagonal phase in accordance with one or more embodiments of the present disclosure.

Reference will now be made in detail to embodiments of a zeolite composite catalyst comprising a mesostructure comprising at least one disordered mesophase and at least one ordered mesophase. In one embodiment, the ordered mesophase is a hexagonal mesophase, and the disordered mesophase comprises a hexagonal mesophase. Without being bound by theory, composite catalyst with ordered and disordered mesophase formation provides improved transalkylation catalyst activity, which provides improved yield of xylenes as compared to zeolite beta and or typical zeolite beta/MCM-41 composite zeolites. As defined, "ordered mesophase" means a crystalline zeolite uniform arrangement of mesopores, where "mesopores" have an average pore diameter between 2 and 50 nanometers. As defined, "disordered mesophase" means a non-uniform arrangement of pores, where mesopores have an average pore diameter between 2 and 50 nanometers. As defined, "ordered/disordered phase" means the surface has a combination of at least one ordered mesophase and at least one disordered mesophase as shown in the transmission electron microscopy (TEM) image of FIG. 9.

In one embodiment, the zeolite composite catalyst may comprise a silica-alumina compound. In another embodiment, the silica-alumina compound may comprise a molar ratio of $SiO_2/Al_2O_3$ of at least 30. Moreover, the molar ratio of $SiO_2/Al_2O_3$ may be from 30 to 100, or from 40 to 80.

In one embodiment, the zeolite composite catalyst may comprise zeolite beta. Zeolite beta is a complex intergrowth family, whose desilication stability is lower than ZSM-5 and mordenite. A commercial embodiment of the zeolite beta is HSZ-940NHA, available from Tosoh Corporation, Japan. In addition, the mesoporous zeolite of the catalyst precursor may comprise at least additional metal or metal oxide in the framework or matrix of the zeolite catalyst. The additional metal or metal oxide in the framework of the zeolite composite catalyst may include zirconium, germanium, tin, or combinations thereof. While various amounts are considered suitable, the molar ratio of silica to the additional metal components (e.g., germanium, zirconium, tin, or combinations thereof) may be from 5 to 100, or from 20 to 100.

Moreover, the zeolite composite catalyst may also comprise at least one additional zeolite, for example, medium or large pore zeolites selected from the group of mordenite, ZSM-5, ZSM-11, ZSM-12, ZSM-22, ZSM-23, MFI topology zeolite, NES topology zeolite, EU-1, MAPO-36, SAPO-5, SAPO-11, SAPO-34, and SAPO-41. For purposes of this disclosure small pore zeolites have a pore size of 3-5 angstroms (Å), medium pore zeolites have a pore size of 5-6 Å, and large pore zeolites have a pore size of 6-8 Å. Without being limited to theory, this may allow the zeolite composite catalyst to maintain the acidity advantage of the medium or large pore zeolite while inheriting pore structure qualities of the mesoporous materials. The amount of this second zeolite may range from 10 to 90 wt % of the total zeolite composite catalyst amount in the final dried and calcined form. The acidity is defined by the ratio of silica to alumina groups in the particular zeolite composite catalyst. The zeolite composite catalyst has an intermediate acidity. For purposes of this disclosure a silica to alumina ratio less than 20 is considered high acidity, a silica to alumina ration in the range of 30 to 100 is considered an intermediate acidity, and a silica to alumina ratio of more than 100 is considered a low acidity.

Moreover, the zeolite composite catalysts may be impregnated with active metals for catalysis, for example, active metals selected from the group consisting of molybdenum, chromium, platinum, nickel, platinum, palladium, or combinations thereof. In one embodiment, the active metal is molybdenum. The metal component may exist within the final catalytic composite as a compound, such as an oxide, sulfide or halide, in chemical combination with one or more of the other ingredients of the composite, or as an elemental metal. The active metal component may be present in the final zeolite composite catalyst in any amount that is catalytically effective, generally comprising 0.01 to 5 wt % of the final catalyst calculated on an elemental basis.

As described in the synthesis discussion as follows, the zeolite composite catalyst may include a zeolite beta/MCM-41 structure produced from a zeolite beta precursor. In at least one embodiment, the zeolite composite catalyst comprises less than 20% of MCM-41 mesoporous content formed from the zeolite beta precursor.

From a property standpoint, the zeolite composite catalyst may have a surface area defined by a Brunauer-Emmett-Teller (BET) analysis of at least 600 meters$^2$/g (m$^2$/g), or a BET surface area of at least 700 m$^2$/g. Further, the zeolite composite catalyst may have an external surface area of at least 300 m$^2$/g, or an external surface area of at least 350 m$^2$/g.

In one or more embodiments, the zeolite composite catalyst may have a total pore volume of 0.20 to 3.0 cm$^3$/g, or 0.30 to 1.0 cm$^3$/g. Moreover, the zeolite composite catalyst may have a total pore volume of at least 0.30 cm$^3$/g, or of at least 0.40 cm$^3$/g, or at least 0.50 cm$^3$/g. In another embodiment, the zeolite composite catalyst may have an average pore diameter of at least 30 angstroms (3 nanometers).

Figure 1:
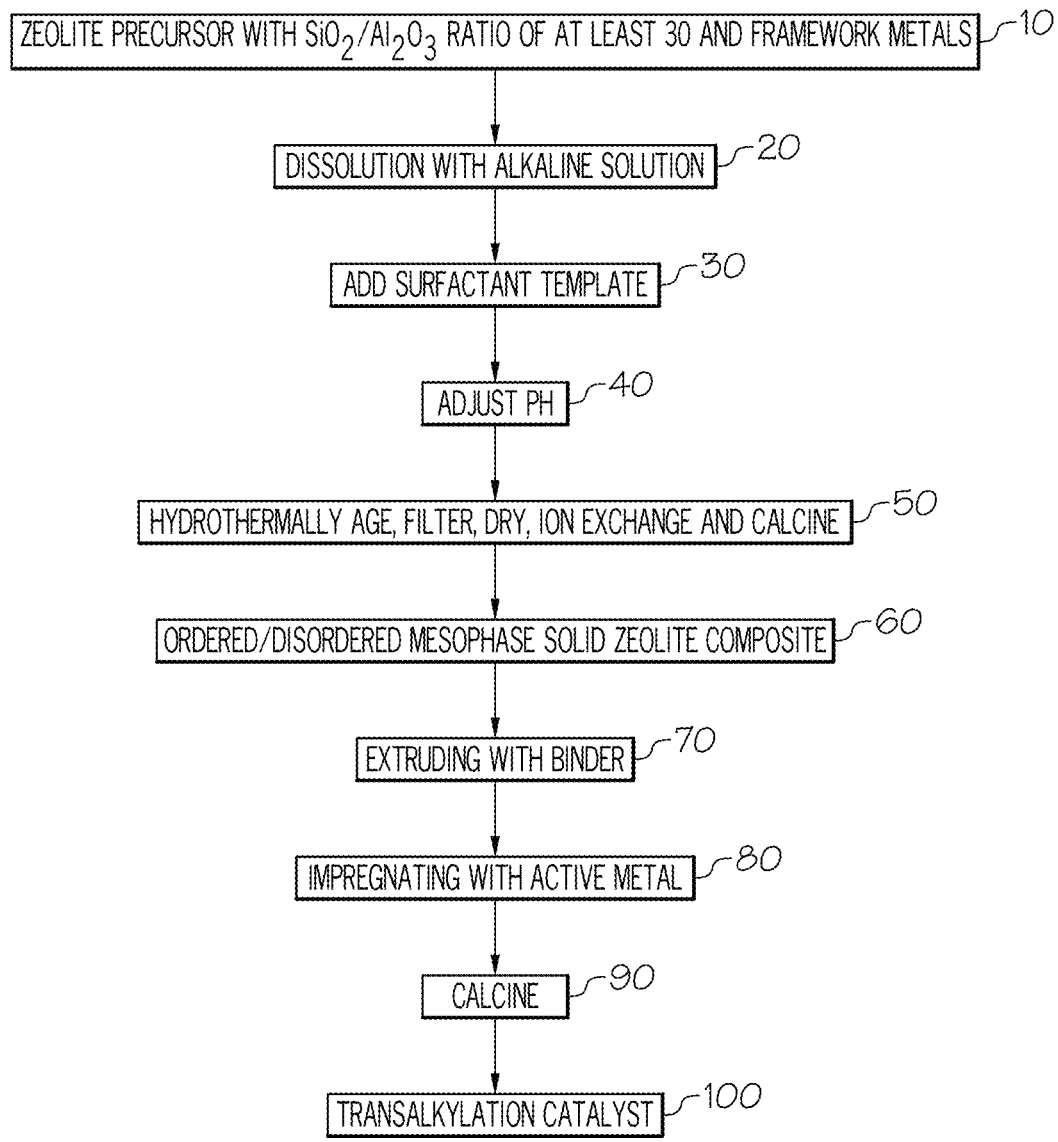
FIG. 1 is a flow chart depicting the synthesis of a zeolite composite catalyst in accordance with one or more embodiments of the present disclosure.

Referring to FIG. 1, the method of producing the zeolite composite catalyst may comprise the steps of providing a catalyst precursor 10 comprising a mesoporous zeolite having a molar ratio of SiO$_2$/Al$_2$O$_3$ of at least 30 and dissolving in an alkaline solution while heating, stirring, or both to yield a dissolved zeolite solution 20. In one embodiment, the catalyst precursor comprises zeolite beta to yield the zeolite beta precursor. Additionally, the catalyst precursor may comprise zeolite beta and at least one additional mesoporous zeolite selected from the group consisting of mordenite, ZSM-22, ZSM-12, and combinations thereof to yield an alternate zeolite beta precursor.

The dissolving step, also called desilication, may be conducted in the presence of a surfactant 30, where the surfactant is often called a templating agent for the zeolite catalyst. While the FIG. 1 embodiment shows templating surfactant, it is contemplated in other embodiments that surfactant is absent. For example and not by way of limitation, the surfactant is a cationic surfactant. The cationic surfactant may include a quaternary ammonium compound. For example and not by way of limitation, the quaternary ammonium cationic surfactant may be cetyltrimethyl ammonium bromide (CTAB). Various amounts of surfactant are contemplated for inclusion in the catalyst precursor. For example, the catalyst precursor may include 1 weight % to 10 weight % surfactant, for example CTAB, or 2 weight % to 8 weight % surfactant, for example CTAB.

During conventional desilication, the mesoporosity in the zeolite is generated by desilication using standard conditions. For example, desilication may be performed using 0.2 M NaOH with 30 min of stirring at 65° C. By this process, one third of catalyst is lost due to desilication; however, the present method utilizes that desilicated source to generate mesoporosity using the surfactant template.

Further as shown in FIG. 1, the dissolution may occur slowly in the presence of a surfactant template by gradual heating for 24 hours. By another method, the desilication can also take place in the absence of a surfactant template. In one embodiment, the desilication may occur in the absence of a surfactant template by stirring for 30 minutes. The filtrate is collected and mesopores are generated using a template mediated technique. In this way, the wasted desilicated source is utilized to produce the mesophases. Various heating processes or elements are contemplated. For example, the heating may be hydrothermal heating. In one or more embodiment, the hydrothermal heating may occur at a temperature of 50 to 150° C., or a temperature of 90 to 110° C. Furthermore, the duration of hydrothermal heating may range from 30 minutes to 24 hours.

Various alkaline solutions are contemplated for the desilication. In one embodiment, the alkaline solution may comprise NaOH. In specific embodiments, the alkaline solution may comprise 0.01 to 0.2 Molarity (M) NaOH, 0.05 to 0.2 Molarity (M) NaOH, or 0.05 to 0.1 M NaOH. Without being bound by theory, it is surprisingly discovered that controlling the molarity of the NaOH is a parameter that impacts the ordered/disordered phase mesostructure of the zeolite composite catalyst.

Referring again to FIG. 1, the method may comprise the step 40 of adjusting the pH of the dissolved zeolite solution. The adjusting of the pH is performed by an acidic solution. Various acids are contemplated. In one embodiment, the acidic solution comprises sulfuric acid. In one embodiment the pH is adjusted to 8 to 10.

Next, various additional steps 50 may be utilized, for example, hydrothermal aging, filtering, washed drying, ion-exchanging and calcining the pH adjusted dissolved zeolite solution. The hydrothermal aging may involve maintaining the pH adjusted dissolved zeolite solution at a temperature of 75 to 125° C. for a duration of 12 to 48 hours. During hydrothermal aging, the soluble aluminosilicate species are hydrothermally condensed to form mesophases. The ion exchange may occur in the presence of a nitrate solution, for example and not by way of limitation, a solution comprising NH$_4$NO$_3$. Moreover, it is contemplated that the zeolite may be steamed at 600-750° C. for 4 hours. At this stage 60, the solid composite zeolite with ordered/disordered mesophase is formed.

Referring to FIG. 1, the process may also include the step 70 of extruding the solid zeolite composite in the presence of binder. A refractory binder or matrix is optionally utilized to facilitate fabrication of the catalyst, to provide strength, and to reduce fabrication costs. Suitable binders include inorganic oxides, such as one or more of alumina, magnesia, zirconia, chromia, titania, boric, phosphate, zinc oxide and silica. In one embodiment, the binder is an alumina based binder. One commercial embodiment of the alumina binder is Cataloid AP-3, obtained from Catalysts & Chemicals Industries Co., Ltd (CCIC), Japan. The zeolites may be mixed in dry powdered form with the alumina binder in aqueous form to yield a homogeneous mixture, thus ensuring homogeneous composition of the extrudates formed. In one or more embodiments, the ratio by weight of solid zeolite composite to binder is 4 to 1, or 3 to 1. The extrusion with binder step 70 may be conducted at a temperature of 100 to 150° C. for a duration of 30 minutes to 2 hours.

Next, the process may comprise the step 70 of impregnating solid zeolite composite with one or more active metals prior to a calcining step. The one or more active metals are selected from the group consisting of molybdenum (Mo), platinum (Pt), rhenium (Re), nickel (Ni), and combinations thereof. In one embodiment, the active metal may comprise 2 to 6% by weight molybdenum. Optionally, the zeolite composite may be dried after wet impregnation for at least 2 hours at 100° C.

Referring again to FIG. 1, another calcining step 90 may be utilized to produce the zeolite composite catalyst, which is effective as a transalkylation catalyst 100. The calcining step may occur for 4 to 8 hours at a temperature of 400 to 500° C., or for 4 hours at a temperature of 400° C.

Further as stated above, the present zeolite composite catalyst is a transalkylation catalyst suitable for converting $C_{9+}$ alkyl aromatic hydrocarbons to a product stream comprising benzene, toluene, and xylene, particularly to commercially valuable xylenes. The feed stream to the conversion process generally comprises alkylaromatic hydrocarbons in the carbon number range $C_9$ to $C_{11+}$ that may include, for example, such hydrocarbons as propylbenzenes, ethylmethylbenzenes, tetramethylbenzenes, ethyldimethylbenzenes, diethylbenzenes, methylpropylbenzenes, and mixtures thereof. The heavy aromatics feed stream, characterized mainly by $C_{9+}$ aromatics, permits effective transalkylation of light aromatics such as benzene and toluene with the heavier $C_{9+}$ aromatics to yield additional $C_8$ aromatics, such as xylenes. The heavy aromatics stream preferably comprises at least 90 wt. % $C_9$ aromatics, and may be derived from the same or different known refinery and petrochemical processes, and may be recycled from the separation of the product from transalkylation.

Figure 2:
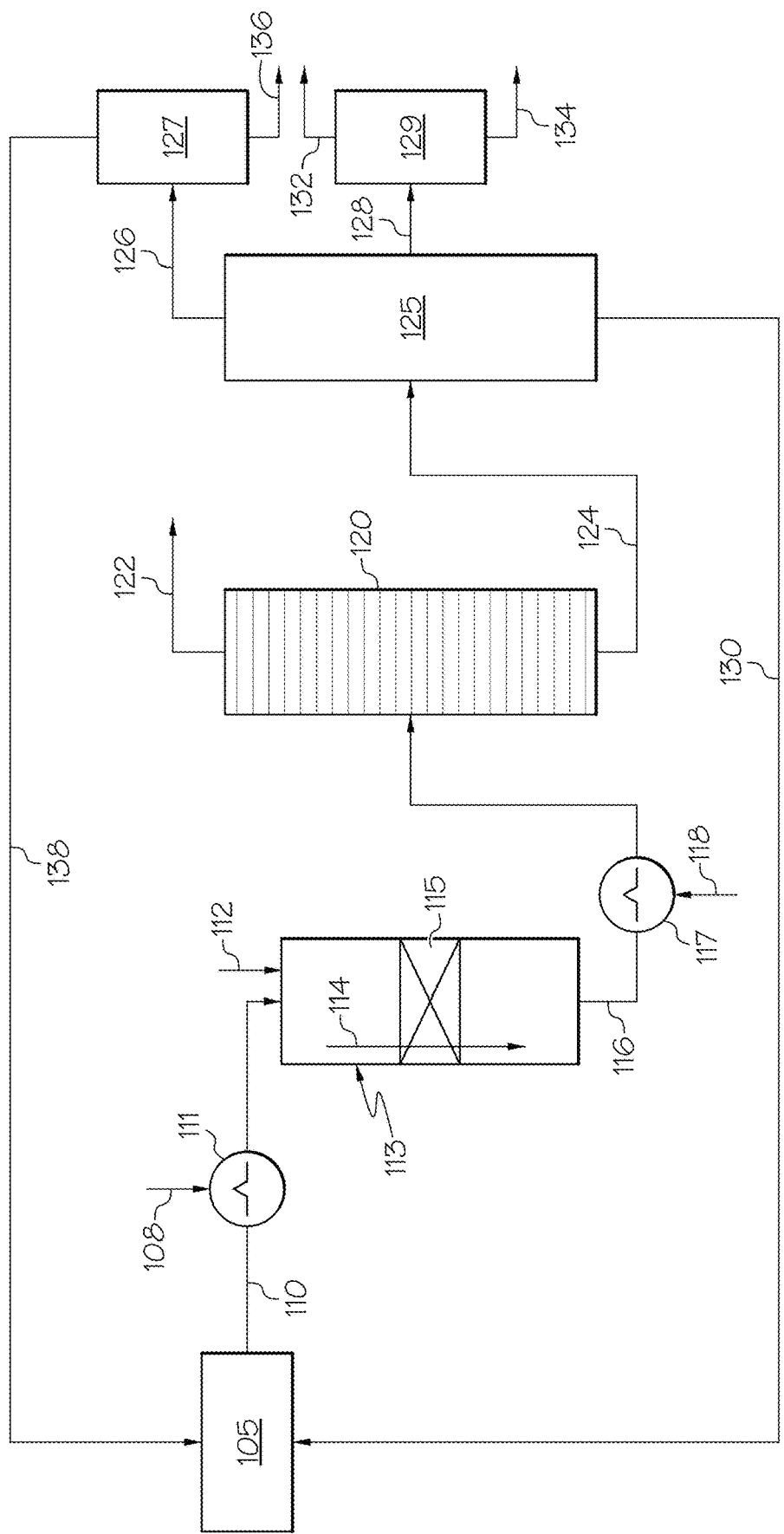
FIG. 2 is a schematic illustration depicting the conversion of heavy reformate into xylenes in accordance with one or more embodiments of the present disclosure.

Referring to the embodiment of FIG. 2, the method of using the zeolite composite catalyst as a transalkylation catalyst may optionally include heating a feed 110 comprising $C_{9+}$ alkylaromatic hydrocarbons from a feed source 105 with a heater unit 111. As shown, the heater unit 111 may be a heat exchanger which receives a heated stream 108, for example, a heated water stream to heat the feed 110 prior to delivery to the reactor system 113. Other methods of heating the feed are contemplated.

The reactor system may include a single reactor 113 with zeolite composite catalyst used in transalkylation catalyst zone 115 as shown in FIG. 2, or may include multiple reactors or stages. The reactor 113 is depicted as a downflow 114 reactor but that is one of many possibilities. In the embodiment of FIG. 2, the reactor 113 has a fixed cylindrical bed of catalyst; however, other reaction configurations utilizing moving beds of catalyst or radial-flow reactors or fluidized bed may be employed. Prior to the feed being delivered, the zeolite composite catalyst in transalkylation catalyst zone 115 may be reduced, for example, reduced with hydrogen gas 112. In one embodiment, the zeolite composite catalyst is reduced by hydrogen gas 112 at a temperature of 350 to 450° C., or 400° C.

Referring again to FIG. 2, the feed stream 110 contacts the reduced composite zeolite catalyst and hydrogen 112 in the transalkylation catalyst zone 115 of the reactor 113. Specifically, the feed 110 is transalkylated in the vapor phase and in the presence of hydrogen 112. The hydrogen 112 may be delivered with the feed stream 110 in an amount from 0.1 to 10 moles of hydrogen per mole of alkylaromatics. This ratio of hydrogen to alkylaromatics is also referred to as the hydrogen-to-hydrocarbon ratio. The transalkylation results in the production of a transalkylation effluent stream 116 comprising product hydrocarbons, specifically, hydrocarbons having mixed xylene content, as well as unconverted feed, toluene, and benzene. Various conditions are contemplated for the reactor 113. Specifically, the transalkylation catalyst zone 115 may include a temperature between 200° C. and 540° C. and moderately elevated pressures of 1.0 MPa to 5.0 MPa. The liquid hourly space velocity (LHSV) is in the range of 1.0 $hr^{-1}$ to 5.0 $hr^{-1}$.

As shown, the transalkylation effluent stream 116 may be cooled using a cooler 117. The cooler 117 may be a heat exchanger, condenser, or any other suitable cooling device familiar to the skilled person. As shown, the cooler 117 is a heat exchanger which includes a cooling stream 118. Next, the transalkylation effluent stream 116 may be fed to a stripper column 120, where $C_1$-$C_5$ and lighter hydrocarbons 122 are separated from the transalkylation effluent stream 116. Additionally, unreacted feed may be stripped from the transalkylation effluent stream 116.

Referring to FIG. 2, the product 124 of the stripper column 120, which may be discharged from the bottom of the stripper column 120, may include a light recycle stream comprising benzene and toluene, a mixed $C_8$ aromatics product, and a heavy recycle stream. These all may subsequently be separated in one or more reaction vessels 125, 127, 129. The mixed $C_8$ aromatics product 128 can be sent for recovery of p-xylene 132 and other valuable isomers 134. The light recycle stream 126 may undergo benzene and toluene recovery 136 with a portion recycled to the transalkylation zone or the feed source 105. The heavy recycle stream 130 may contain substantially all of the $C_9$ and heavier aromatics and may be partially or totally recycled to the transalkylation reaction zone, or delivered to the feed source 105 for recycle, or removed from the process for disposal or other processing.

EXAMPLES

The described embodiments will be further clarified by the following examples.

For demonstration purposes, the preparation of composite catalysts is provided as follows. The synthesis of Catalyst A, which includes an ordered hexagonal phase, is described in Example 1. The preparation of composite Catalyst B with disordered hexagonal mesophase is described in Example 2. The preparation of composite Catalyst C with ordered/disordered hexagonal mesophase is presented in Example 3. The performance of Catalyst A was compared with a physical mixture of two zeolites which are constituents of Catalyst A in Example 4. The performance of Catalyst A was compared with one of its constituents (zeolite beta) in Example 5. Example 6 described the preparation of desilicated zeolite beta 40 (Catalyst D). Preparation of metal-loaded composite catalysts (A-1, B-1, C-1, E-1, F-1 and G-1), is described in Example 7. The performance of Catalysts A-1, B-1, C-1, D, E-1, F-1 and G-1 is compared in Example 8. Finally, Example 9 describes the preparation of mesoporous zeolite beta composite catalyst using desilicated filtrate solution.

The catalysts described in these examples are exemplary embodiments only, and are not intended to limit the general description of the composite catalyst covering this invention. In each example, the zeolite beta is HSZ-940NHA, available from Tosoh Corporation, Japan.

Example 1

Preparation of Hierarchical Catalyst A with Ordered Hexagonal Mesophase

Two grams of zeolite beta (Si/Al molar ratio=40) was disintegrated using 0.45 M NaOH solution by gradual heating (without stirring) at 100° C. for 24 hours (h). The heating was carried out in the presence of CTAB (4.45 wt. %). The mixture was cooled down and then the pH was adjusted to 9.0 through the addition of dilute sulfuric acid (2 Normality (N) equivalents/liter). The mixture was then stirred for 24 hours (h) and then aged at 100° C. for 24 h to form a zeolite beta/MCM-41 composite. The solid product was filtered, washed thoroughly using distilled water, dried at 80° C. overnight, then calcined at 550° C. for 6 h to remove the surfactant. The composite material thus obtained was ion-exchanged three times with 0.05 M $NH_4NO_3$ solution at 80° C. for 2 h then calcined at 550° C. for 2 h. The resulting zeolite beta/MCM-41 composite is designated as Catalyst A.

Figure 3:
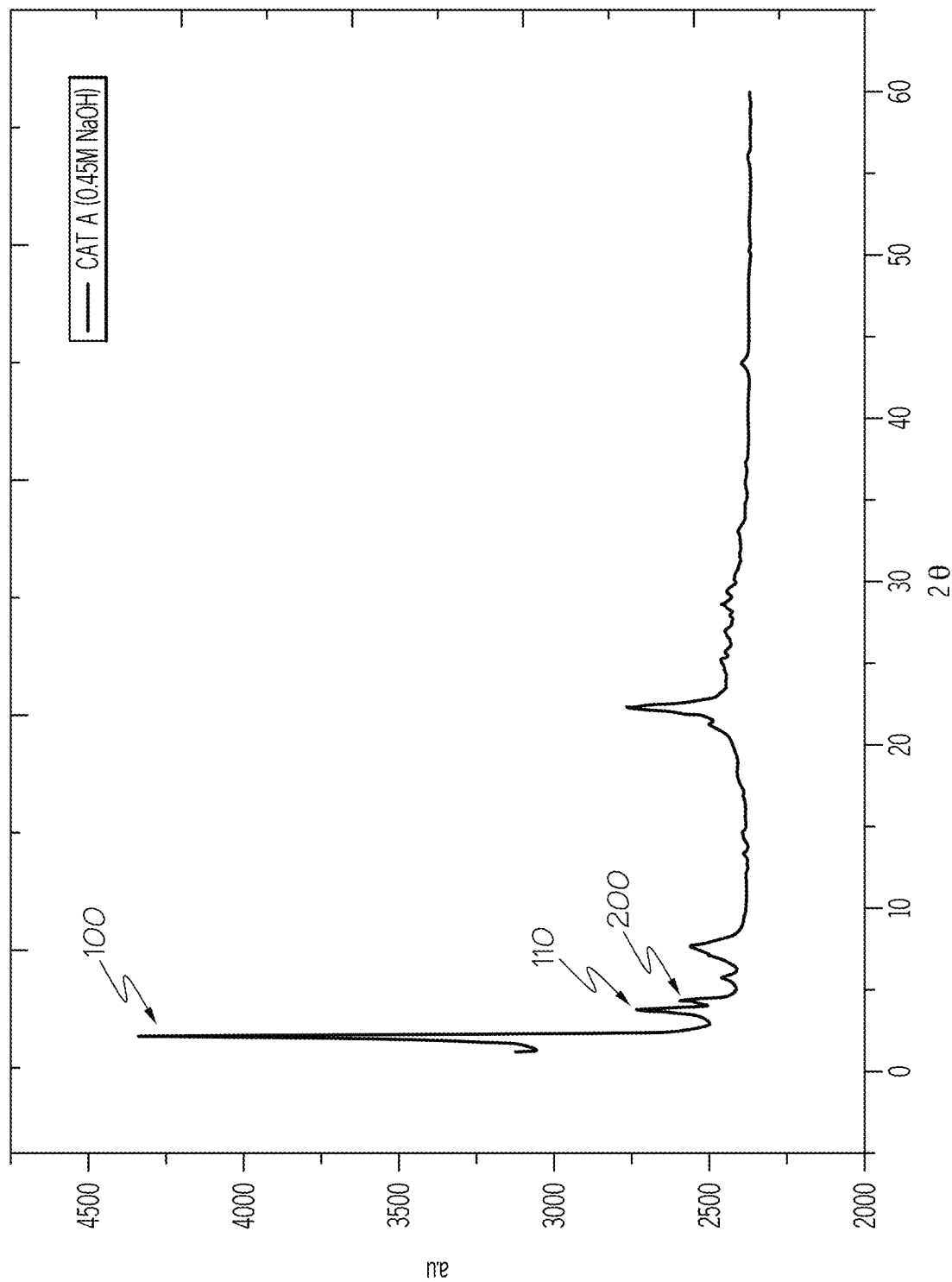
FIG. 3 is an X-Ray Diffraction (XRD) graph of a zeolite composite catalyst with an ordered hexagonal mesophase, which was produced through dissolution of zeolite beta using 0.45 Molarity (M) NaOH solution in the presence of cetyl trimethyl ammonium bromide (CTAB).

As shown in FIG. 3, the dissolution of zeolite beta using 0.45 M NaOH solution in the presence of CTAB leads to the formation of Catalyst A, a typical biporous composite with ordered hexagonal mesophase. In the low X-ray diffraction angle, an intense peak indexed at (100) along with intense higher order diffraction peaks indexed at (110) and (200), corresponding to MCM-41, were observed.

Example 2

Preparation of Composite Catalyst B with Ordered/Disordered Hexagonal Mesophase

Two grams of zeolite beta (Si/Al ratio=40) was disintegrated using 0.1 M NaOH solution by gradual heating (without stirring) at 100° C. for 24 h. The heating was carried out in the presence of CTAB (4.45 wt. %). The mixture was cooled down and then the pH was adjusted to 9.0 through the addition of dilute sulfuric acid (2N). The mixture was then stirred for 24 h and then aged at 100° C. for 24 h to form a zeolite beta/MCM-41 composite. The solid product was filtered, washed thoroughly using distilled water, dried at 80° C. overnight, then calcined at 550° C. for 6 h to remove the surfactant. The composite material thus obtained was ion-exchanged three times with 0.05 M $NH_4NO_3$ solution at 80° C. for 2 h then calcined at 550° C. for 2 h. The resulting zeolite beta/MCM-41 composite is designated as Catalyst B.

Figure 4:
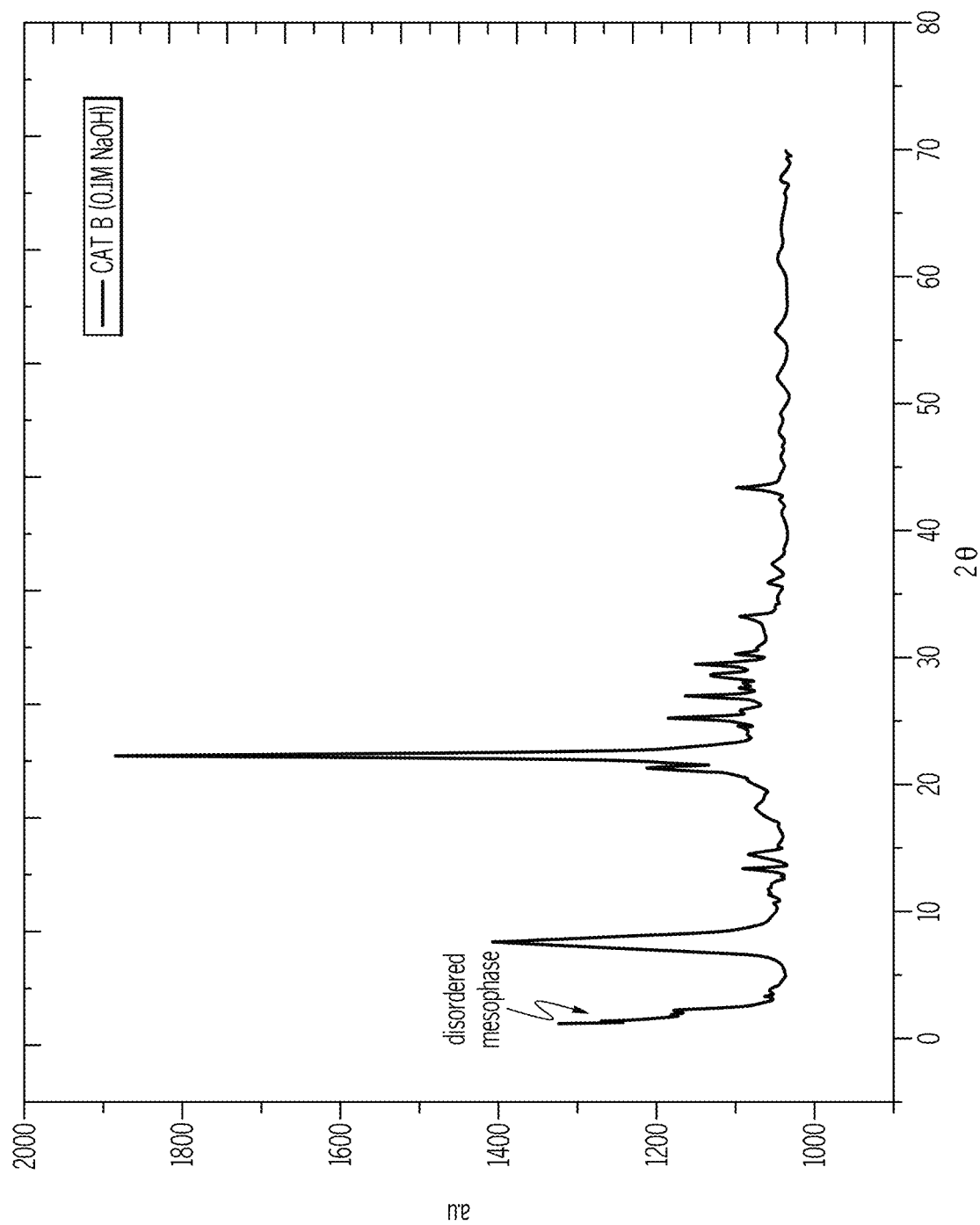
FIG. 4 is an XRD graph of a zeolite composite catalyst having an ordered hexagonal mesophase and a disordered hexagonal mesophase, which was produced through the dissolution of zeolite beta using 0.1 M NaOH solution in the presence of CTAB in accordance with one or more embodiments of the present disclosure.

The dissolution of zeolite beta using 0.1 M NaOH solution in the presence of CTAB leads to the formation of mesopores with disordered hexagonal mesophase as shown in FIG. 4. The XRD pattern indicates the formation of mesoporous zeolite beta containing highly zeolite beta character along with a disordered hexagonal mesophase.

Example 3

Preparation of Composite Catalyst C with Ordered/Disordered Hexagonal Mesophase

Two grams of zeolite beta (Si/Al ratio=40) was disintegrated using 0.2 M NaOH solution by gradual heating (without stirring) at 100° C. for 24 h. The heating was carried out in the presence of CTAB (4.45 wt. %). The mixture was cooled down and then the pH was adjusted to 9.0 through the addition of dilute sulfuric acid (2N). The mixture was then stirred for 24 h and then aged at 100° C. for 24 h to form a zeolite beta/MCM-41 composite. The solid product was filtered, washed thoroughly using distilled water, dried at 80° C. overnight, then calcined at 550° C. for 6 h to remove the surfactant. The composite material thus obtained was ion-exchanged three times with 0.05 M $NH_4NO_3$ solution at 80° C. for 2 h then calcined at 550° C. for 2 h. The resulting zeolite beta/MCM-41 composite is designated as Catalyst C. Table 1 includes selected properties of Catalyst C.

TABLE 1

Catalyst C Data

| Catalyst | BET Surface Area (m²/g) | External Surface Area (m²/g) | Average Pore Diameter (Å) | Total Pore Volume (cm³/g) | t-plot Micropore Volume (cm³/g) |
|---|---|---|---|---|---|
| Zeolite Beta/MCM-41 (Catalyst C) | 714 | 388 | 33.47 | 0.59 | 0.16 |

Figure 5:
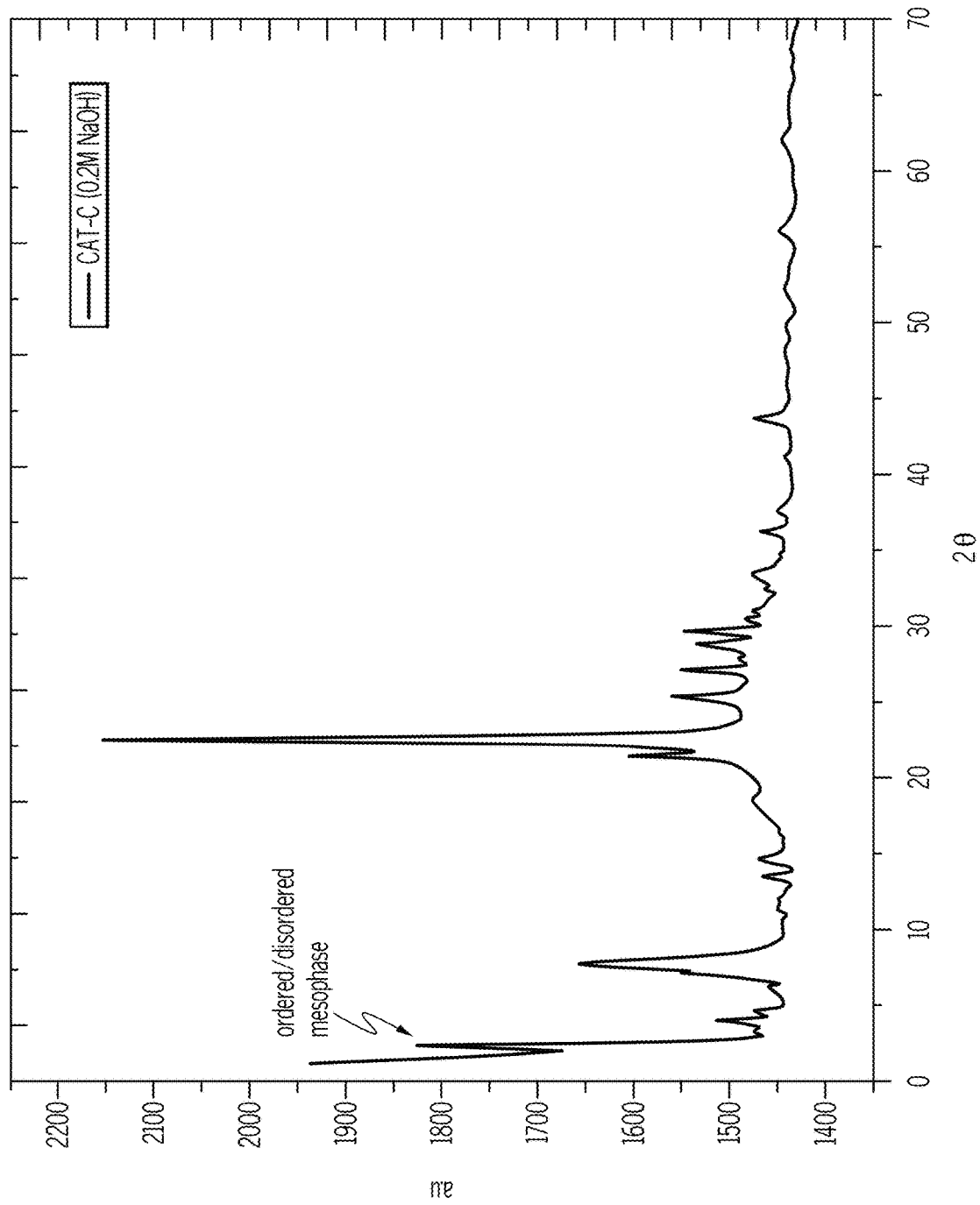
FIG. 5 is an XRD graph of a zeolite composite catalyst having an ordered hexagonal mesophase and a disordered hexagonal mesophase, which was produced through the dissolution of zeolite beta using 0.2 M NaOH solution in the presence of CTAB in accordance with one or more embodiments of the present disclosure.

As shown in FIG. 5, the dissolution of zeolite beta using 0.2 M NaOH solution in the presence of CTAB leads to the formation of a less intense hexagonal phase containing ordered/disordered mesophase.

Figure 6:
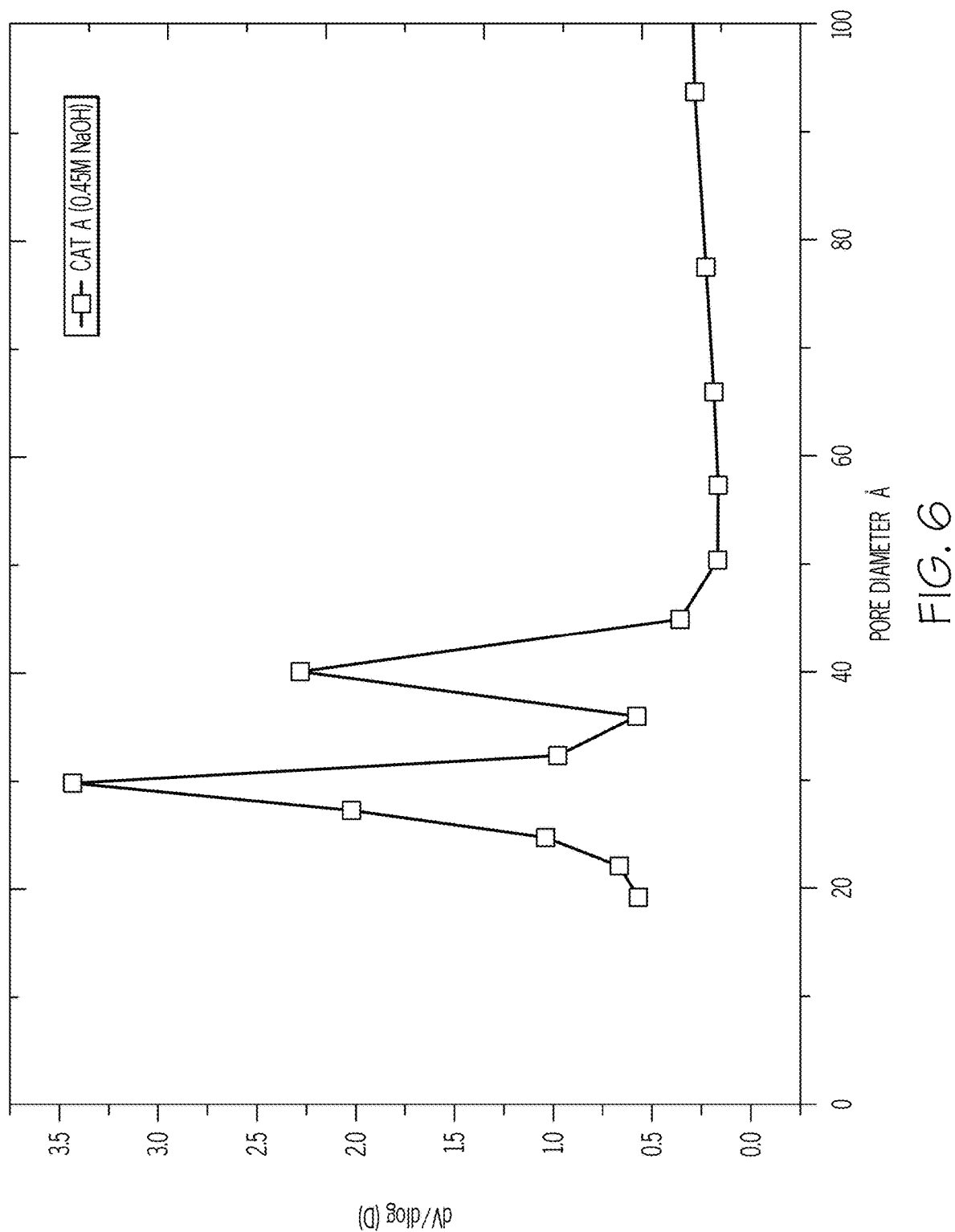
FIG. 6 is a graph illustrating the pore size distribution of the catalyst depicted in FIG. 3.
Figure 7:
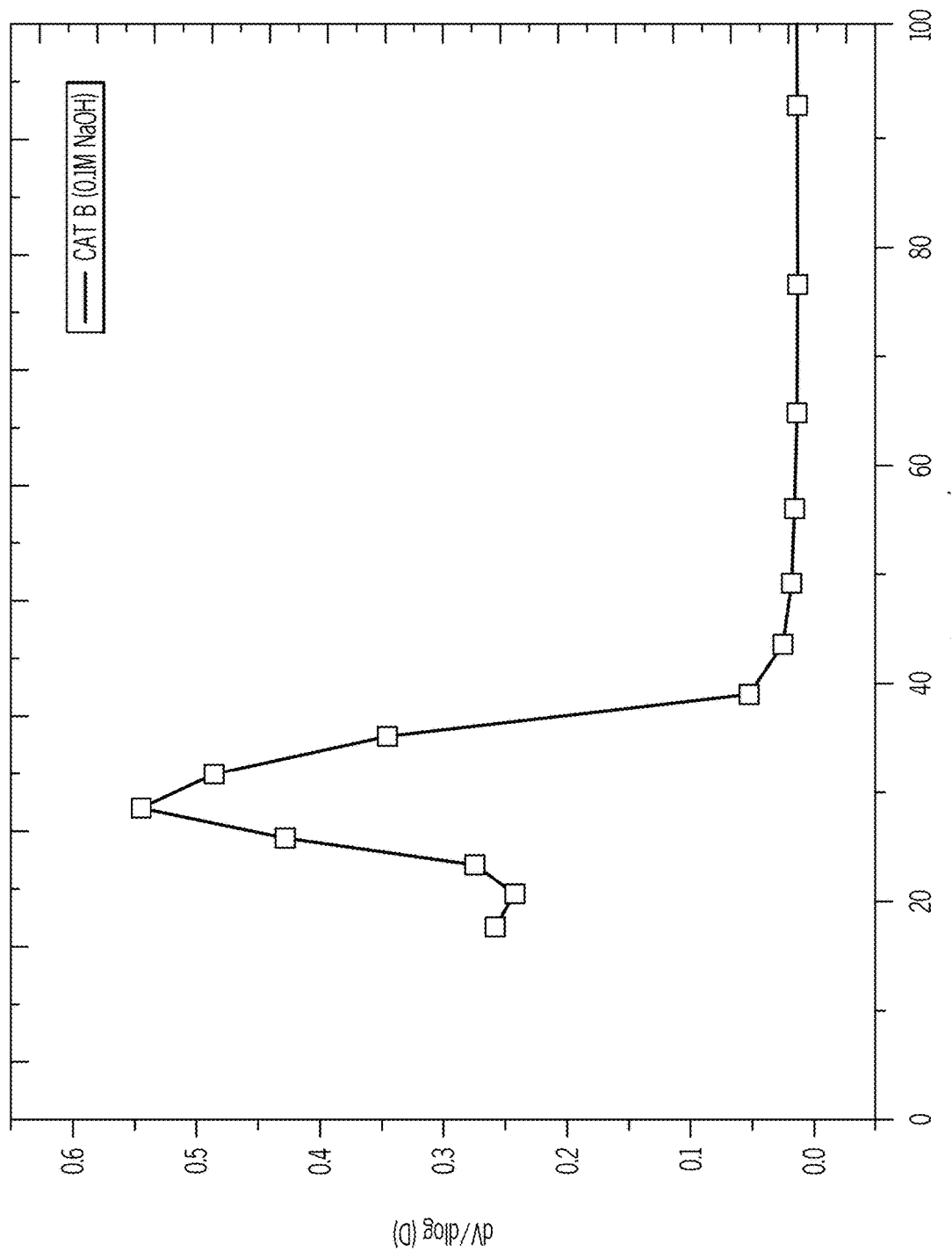
FIG. 7 is a graph illustrating the pore size distribution of the catalyst depicted in FIG. 4 in accordance with one or more embodiments of the present disclosure.
Figure 8:
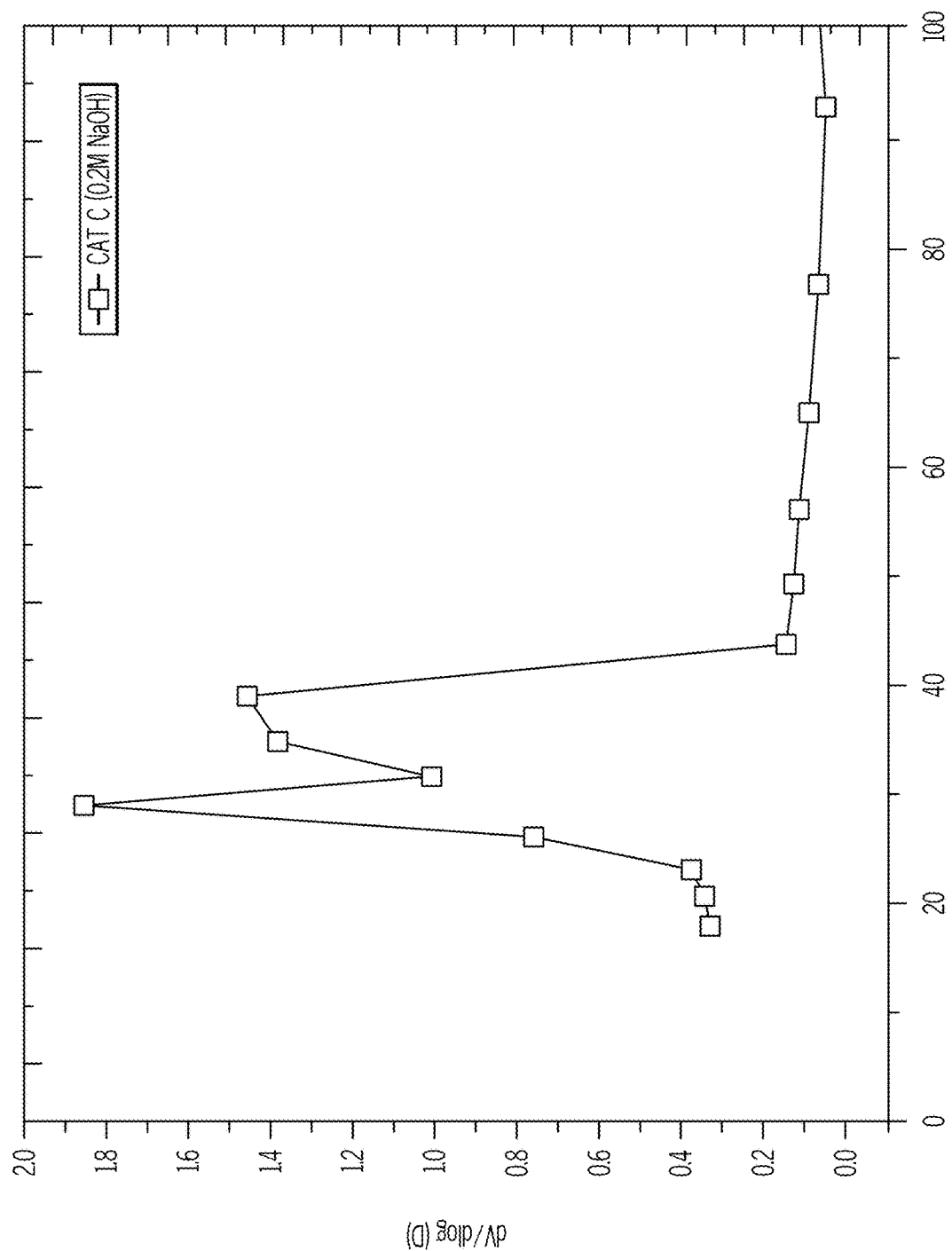
FIG. 8 is a graph illustrating the pore size distribution of the catalyst depicted in FIG. 5 in accordance with one or more embodiments of the present disclosure.

Referring to FIGS. 6-8, catalyst A exhibits narrow mesopore size distribution (FIG. 6). However, the pore size distribution of disordered mesophase containing Catalyst B (FIG. 7) and the ordered/disordered mesophase Catalyst C shows that the pores are not uniformly distributed (FIG. 8) as compared to typical biporous composite.

Example 4

Comparison of Catalyst A with Physical Mixture of its Constituents

The activity of Catalyst A for transalkylation reaction was tested in a bench top reaction system using a feedstock containing 1,2,4-trimethyl benzene and toluene in a 1:1 molar ratio. A catalyst made by physically mixing zeolite beta and MCM-41 in equal proportion (Catalyst PMBM) was also tested in order to demonstrate effectiveness of the composite catalyst for $C_9$ conversion and xylene yield. The catalytic test consisted of loading a vertical reactor with 2.0 milliliters (ml) of the catalyst in the middle of the reactor together with inert alumina balls in the lower and upper parts of the reactor. The total volume of the reactor was 5 ml. The catalyst was activated and reduced under a 50 ml/min flow of pure hydrogen gas at 400° C. and was kept at this temperature for 2 hours. Then, the pressure of the reactor was increased to 20 bar and the flow of feedstock was started at 4.8 ml/h. The reaction was allowed to run 3 hours at this temperature before collecting the product sample.

The reaction product was directly injected into an on-line gas chromatograph equipped with a flame ionization detector. The hydrocarbon separation was carried out on a 50 meter (m) long and 0.15 millimeters (mm) diameter column under temperature programmed conditions. The components were separated according to their boiling points. The components were identified using a calibration that was accomplished using a standard hydrocarbon mixture sample having components of a known composition. The composition of the gaseous product was analyzed off-line by a gas chromatograph equipped with a flame ionization detector and thermal conductivity detector. The gaseous hydrocarbons and hydrogen were analyzed by a 50 m long capillary column.

From the data shown in Table 2 as follows, Catalyst A shows a substantially higher yield of xylenes as compared to the physical mixture of zeolite beta and MCM-41 (Catalyst PMBM) under identical process conditions. These results indicate that the composite catalyst containing zeolite beta and MCM-41 possesses a unique structure which performs differently from a mere mixture of its constituents.

TABLE 2

Performance Comparison of Catalyst A with Physical Mixture of its Constituents

| Product Analysis | Catalyst A | PMBM |
|---|---|---|
| Alkanes | 0.66 | 1.57 |
| Benzene | 5.58 | 2.85 |
| Toluene | 39.48 | 20.08 |
| EB | 0.33 | 0.00 |
| p-Xylene | 9.35 | 6.27 |
| m-Xylene | 20.86 | 13.75 |
| o-Xylene | 9.09 | 6.23 |
| 135-TMB | 3.66 | 8.69 |
| 124-TMB | 8.74 | 23.59 |
| 123-TMB | 1.24 | 4.02 |
| 1245-TeMB | 0.39 | 4.85 |
| 1235-TeMB | 0.51 | 6.45 |
| 1234-TeMB | 0.11 | 1.65 |
| 124-TMB Conversion (wt. %) | 84.1 | 57.1 |
| Xylenes Yield (wt. %) | 39.3 | 26.3 |

Example 5

Comparison of Catalyst A with Zeolite Beta

The activity of Catalyst A for transalkylation reaction was tested in a bench top reactor using industrial heavy reformate feedstock. A sample of zeolite beta was also tested in order to demonstrate effectiveness of the composite catalyst for $C_9$ conversion and xylene yield. The procedure used for determination of catalytic activity was same as described in Example 4, expect for the feedstock which was industrial heavy reformate feedstock. The composition of the heavy reformate is presented in Table 3.

TABLE 3

Heavy Reformate Composition

| Major Hydrocarbons | Amount (wt. %) |
|---|---|
| Isopropyl benzene | 1.8 |
| n-Propyl-benzene | 4.4 |
| 1-Methyl, 3-ethyl benzene | 18.5 |
| 1-Methyl, 4-ethyl benzene | 9.1 |
| 1,3,5-trimethyl benzene | 10.1 |
| 1-Methyl,2-ethyl benzene | 6.5 |
| 1,2,4-trimethyl benzene | 39.1 |
| 1,2,3-trimethyl benzene | 6.6 |
| Total $C_9$ Components | 96.1 |
| Total $C_{10}$ Components | 3.9 |

From the product compositional data shown in Table 4, Catalyst A provided higher yield of xylenes compared to zeolite beta. The data also shows higher percent conversion of individual $C_9$ hydrocarbons, especially the major ones listed in Table 3.

TABLE 4

Performance Comparison of Catalyst A with Zeolite Beta

| | Catalyst | |
|---|---|---|
| Product Analysis | Zeolite Beta | A |
| Light Alkanes | 1.69 | 1.63 |
| Benzene | 1.01 | 1.75 |
| Toluene | 9.00 | 12.99 |
| EB | 2.39 | 2.50 |
| p-Xylene | 5.17 | 7.13 |
| m-Xylene | 11.13 | 15.72 |
| o-Xylene | 4.81 | 6.75 |
| 135 TMB | 11.35 | 8.63 |
| 124 TMB | 24.37 | 18.89 |
| 123 TMB | 3.14 | 2.34 |
| 1M2EB | 1.60 | 1.29 |
| 1M3EB | 2.76 | 2.19 |
| 1M4EB | 7.04 | 5.63 |
| 1245 TeMB | 2.74 | 1.95 |
| 1235 TeMB | 2.99 | 2.27 |
| 1234 TeMB | 0.68 | 0.45 |
| DEBs | 4.27 | 5.70 |
| Other C10+ | 3.85 | 2.19 |
| $C_9$+ Conversion (wt. %) | 56.8 | 66.7 |
| Xylenes Yield (wt. %) | 21.1 | 29.6 |

Example 6

Preparation of Desilicated Zeolite Beta 40 (Catalyst D)

Two grams of zeolite beta (Si/Al molar ratio=40) was desilicated using 0.2 M NaOH solution by stirring at 65° C. for 30 min. The mixture was cooled down and the solid product was filtered, washed thoroughly using distilled water, and dried at 80° C. overnight. The material thus obtained was ion-exchanged three times with 0.05-M $NH_4NO_3$ solution at 80° C. for 2 h then calcined at 550° C. for 2 h. The resulting desilicated zeolite is designated as Catalyst D.

Example 7

Preparation of Metal-Loaded (Pt, Mo) Composite Catalysts

From the Examples 1-3, the composite catalyst A was found to be active for transalkylation. In order to improve the performance, the catalysts with hexagonally ordered and disordered pore-structures were prepared and active metal(s) were loaded on composite Catalysts A, B and C.

Examples of such molybdenum-loaded composite catalysts are designated as Catalyst A-1 (4.0 wt. % Mo), B-1 (4.0 wt. % Mo), and C-1 (4.0 wt. % Mo). The activity was compared with conventional desilicated Zeolite Beta 40 (Catalyst D). A catalyst loaded with platinum on Catalyst A is designated as Catalyst E-1 (2.0 wt. % Pt). A catalyst loaded with molybdenum on Catalyst A is designated as Catalyst F-1 (2.0 wt. % Mo). A catalyst loaded with platinum and molybdenum on Catalyst A is designated as Catalyst G-1 (1.5 wt. % Mo+0.5 wt. % Pt). The incipient wetness impregnation method was applied for metal-loading and its procedure is summarized as follows:

Step 1: One gram of catalyst A was soaked in 1.72 grams (g) of deionized water for pore volume saturation; Step 2: 0.0397 g of tetraamine platinum nitrate was dissolved in 1.72 g of deionized water; Step 3: One gram of catalyst A was then added and homogeneously mixed with a dissolved platinum or molybdenum solution; and Step 4: The sample was dried overnight at 100° C. followed by calcination at 400° C. for four hours (heating rate was 5° C./min).

In case of bimetallic impregnation, initially 1.5 wt. % Mo was impregnated, dried and then 0.5 wt. % Pt was impregnated. Then the sample was calcined at 400° C. for four hours. The heating rate was 5° C./min.

Example 8

Performance Comparison of Metal-Loaded Catalysts A-1, B-1, C-1, E-1, F-1 and G-1 with Desilicated Catalyst D The activity of catalysts for transalkylation reaction was tested in a bench top reaction system using industrial heavy reformate feedstock. The procedure used for determination of catalytic activity was the same as described in Example 4.

From the product compositional data shown in Table 5 it can be noticed that impregnation of active metal(s) resulted in significant improvement, especially in selectivity towards xylenes. The composition of product obtained over 2% Mo (Catalyst F-1) shows marked reduction in light hydrocarbon yield. It also shows higher TMB conversion and thus improved xylene yield (29.5 wt. %).

TABLE 5

Performance Comparison of Metal-Loaded Catalysts A-1, B-1, C-1, E-1, F-1 and G-1 with desilicated Catalyst D

| | Catalyst D | Catalyst A-1 | Catalyst B-1 | Catalyst C-1 | Catalyst E-1 | Catalyst F-1 | Catalyst G-1 |
|---|---|---|---|---|---|---|---|
| Product Composition (wt. %) | | | | | | | |
| Light Hydrocarbons | 7.00 | 1.63 | 2.95 | 2.14 | 12.76 | 1.04 | 5.89 |
| Benzene | 1.07 | 1.75 | 1.02 | 1.31 | 0.83 | 1.13 | 1.01 |
| Toluene | 9.83 | 12.99 | 10.80 | 13.56 | 8.34 | 11.01 | 8.68 |
| Ethylbenzene | 1.54 | 2.50 | 1.25 | 0.78 | 0.72 | 1.54 | 0.66 |
| p-xylene | 4.97 | 7.13 | 6.25 | 6.71 | 4.91 | 6.27 | 6.19 |
| m-xylene | 15.35 | 15.72 | 16.86 | 19.34 | 14.57 | 16.66 | 15.64 |
| o-xylene | 5.93 | 6.75 | 7.02 | 7.64 | 5.69 | 6.54 | 6.33 |
| 1-Methyl-2-ethylbenzene | 0.65 | 1.29 | 1.04 | 1.50 | 0.86 | 0.39 | 0.88 |
| 1-Methyl-3-ethylbenzene | 4.20 | 2.19 | 3.32 | 1.79 | 3.15 | 3.70 | 1.90 |
| 1-Methyl-4-ethylbenzene | 1.88 | 5.63 | 1.88 | 1.02 | 1.42 | 2.10 | 1.07 |
| 1,2,3-Trimethylbenzene | 3.12 | 2.34 | 2.75 | 2.85 | 3.30 | 1.66 | 2.93 |
| 1,2,4-Trimethylbenzene | 21.64 | 18.89 | 20.37 | 20.82 | 23.30 | 21.01 | 21.98 |
| 1,3,5-Trimethylbenzene | 9.05 | 8.63 | 8.14 | 7.43 | 9.25 | 7.58 | 7.92 |
| 1,2-Diethylbenzene | 2.54 | 3.10 | 0.63 | 0.90 | 0.00 | 1.01 | 0.96 |
| 1,3-Diethylbenzene | 2.50 | 2.60 | 2.23 | 1.29 | 0.00 | 0.22 | 0.61 |
| 1,2,3,4-Tetramethylbenzene | 0.98 | 0.45 | 1.10 | 1.11 | 0.90 | 0.26 | 1.28 |
| 1,2,3,5-Tetramethylbenzene | 4.02 | 2.27 | 4.93 | 4.58 | 3.81 | 4.83 | 5.71 |
| 1,2,4,5-Tetramethylbenzene | 1.20 | 2.74 | 2.98 | 2.77 | 2.91 | 2.96 | 3.43 |
| Others ($C_{10}$+ aromatics) | 2.53 | 2.19 | 4.49 | 2.46 | 3.27 | 10.09 | 6.93 |
| Conversion (wt. %) | | | | | | | |
| Trimethylbenzenes | 45.88 | 49.96 | 50.22 | 45.88 | 35.75 | 45.79 | 41.16 |
| Methylethylbenzenes | 76.62 | 78.32 | 85.03 | 76.62 | 84.06 | 81.85 | 88.71 |
| $C_9$+ | 45.69 | 46.14 | 51.48 | 45.69 | 47.83 | 44.19 | 44.40 |
| Xylenes Yield (wt. %) | 26.25 | 30.14 | 33.69 | 26.25 | 25.18 | 29.47 | 28.16 |
| Xylenes Selectivity (%) | 57.45 | 65.32 | 65.44 | 57.45 | 52.64 | 66.69 | 63.42 |

Example 9

Preparation of Mesoporous Zeolite Beta Composite Catalyst Using Desilicated Filtrate Solution Zeolite beta was desilicated by stirring with 60 mL of 0.2 M NaOH solution at 65° C. for 30 min. The solid product was filtered, washed thoroughly using distilled water, dried and ion-exchanged and calcined at 500° C. for 2 h.

The filtrate was collected and used for mesostructure transformation, in the presence of CTAB (2-8 wt. %). The mixture was cooled down and then the pH of the mixture was adjusted to 9.0 through the addition of dilute sulfuric acid (2N). The mixture was then stirred for 24 h and then aged at 100° C. for 24 h to form a hierarchical zeolite beta. The solid product was filtered, washed thoroughly using distilled water, dried at 80° C. overnight, then calcined at 550° C. for 6 h to remove the surfactant. The composite material thus obtained was ion-exchanged three times with 0.05 M NH$_4$NO$_3$ solution at 80° C. for 2 h then calcined at 550° C. for 2 h.

It should be apparent to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

What is claimed is:

1. A method of producing a zeolite composite catalyst comprising:
   dissolving in an alkaline solution a catalyst precursor comprising at least one mesoporous zeolite while heating, stirring, or both to yield a dissolved zeolite solution, where the mesoporous zeolite has a molar ratio of SiO$_2$/Al$_2$O$_3$ of at least 30, where the mesoporous zeolite comprises zeolite beta, and where the alkaline solution is a 0.1 to 0.2 M NaOH solution;
   adjusting a pH of the dissolved zeolite solution;
   aging the pH adjusted dissolved zeolite solution to yield solid zeolite composite from the dissolved zeolite solution; and
   calcining the solid zeolite composite to produce the zeolite composite catalyst, where the zeolite composite catalyst has a mesostructure comprising at least one disordered mesophase and at least one ordered mesophase, and where the zeolite composite catalyst has a surface area defined by a Brunauer-Emmett-Teller (BET) analysis of at least 600 m$^2$/g.

2. The method of claim 1 further comprising extruding the solid zeolite composite with binder.

3. The method of claim 2 where the binder is an alumina based binder.

4. The method of claim 2 where a ratio by weight of the solid zeolite composite to binder is 4 to 1.

5. The method of claim 1 where the ordered mesophase is a hexagonal mesophase.

6. The method of claim 1 where the mesoporous zeolite of the catalyst precursor comprises at least one additional metal or metal oxide.

7. The method of claim 6 where the at least one additional metal or metal oxide is selected from the group consisting of zirconium, germanium, tin, and combinations thereof.

8. The method of claim 1 where the heating is hydrothermal heating.

9. The method of claim 1 where the aging involves maintaining the pH adjusted dissolved zeolite solution at a temperature of 75 to 125° C. for a duration of 12 to 48 hours.

10. The method of claim 1 further comprising ion exchanging the solid zeolite composite.

11. The method of claim 1 where the dissolving is conducted in an absence of surfactant.

12. The method of claim 1 where the dissolving is conducted in presence of surfactant.

13. The method of claim 12 where the surfactant is cetyltrimethyl ammonium bromide.

14. The method of claim 1 where the catalyst precursor further comprises at least one additional mesoporous zeolite selected from the group consisting of mordenite, ZSM-22, ZSM-12, and combinations thereof.

15. The method of claim 1 where the adjusting of the pH is performed by an acidic solution.

16. The method of claim 1 where the zeolite composite catalyst has a pore volume ranging from 0.2 to 3.0 cc/g.

17. The method of claim 1 where a molar ratio of silica to aluminum in the zeolite composite catalyst is from 30 to 100.

18. The method of claim 1 where a molar ratio of silica to germanium, zirconium and tin is from 5 to 100.

19. The method of claim 1 further comprising impregnating solid zeolite composite with one or more active metals prior to calcining step, where the one or more active metals are selected from the group consisting of molybdenum, platinum, rhenium, nickel, and combinations thereof.

20. The method of claim 19 where the active metals comprise molybdenum.

* * * * *